United States Patent [19]

Halling et al.

[11] Patent Number: 5,608,116
[45] Date of Patent: Mar. 4, 1997

[54] PROCESS FOR THE ALKOXYLATION OF FLUORINATED ALCOHOLS

[75] Inventors: Robert A. Halling, Wilmington; Hsu-Nan Huang, Newark, both of Del.

[73] Assignee: E. I. Du Pont de Nemours and Company, Wilmington, Del.

[21] Appl. No.: 405,327

[22] Filed: Mar. 16, 1995

Related U.S. Application Data

[63] Continuation-in-part of Ser. No. 263,091, Jun. 21, 1994.

[51] Int. Cl.$^6$ .................................................. C07C 41/03
[52] U.S. Cl. ................................... 568/615; 568/614
[58] Field of Search ........................................ 568/615

[56] References Cited

U.S. PATENT DOCUMENTS

| | | | |
|---|---|---|---|
| 2,723,999 | 11/1955 | Cowen et al. | 260/615 |
| 3,948,668 | 4/1976 | Hayek et al. | 106/20 |
| 4,404,407 | 9/1983 | Harris | 568/648 |
| 4,478,760 | 10/1984 | Blancou et al. | 558/357 |
| 4,483,941 | 11/1984 | Yang | 502/171 |
| 4,490,561 | 12/1984 | Yang et al. | 568/615 |
| 4,533,759 | 8/1985 | Harris | 568/648 |
| 5,097,090 | 3/1992 | Beck | 568/842 |

FOREIGN PATENT DOCUMENTS

| | | | |
|---|---|---|---|
| 0161459 | 4/1985 | European Pat. Off. | C07C 43/11 |
| 2459900 | 12/1974 | Germany | C08G 65/12 |
| 2153373 | 8/1985 | United Kingdom | C07C 65/26 |
| WO95/35272 | 12/1995 | WIPO | C07C 43/11 |

OTHER PUBLICATIONS

*Derwent Publications Abstract* "Surface Active Alkoxylated Fluoro Alcohols—Useful for Making Fluoropolymers for Textile Finishing" & DD,A,111 522 (Greiner A.), 20 Feb. 1975.

*Primary Examiner*—Porfirio Nazario-Gonzalez
*Assistant Examiner*—Dwayne C. Jones

[57] ABSTRACT

The present invention relates to the preparation of fluoroalkylalkoxylates in which one reacts at least one fluorinated alcohol with at least one alkylene epoxide in the presence of a novel catalyst system comprising an iodine source and an alkali metal borohydride.

16 Claims, No Drawings

PROCESS FOR THE ALKOXYLATION OF FLUORINATED ALCOHOLS

CROSS-REFERENCE TO RELATED APPLICATIONS

This is a continuation-in-part of application Ser. No. 08/263,091 filed 21 Jun. 1994 now allowed.

FIELD OF THE INVENTION

The present invention relates to a process for the preparation of fluoroalkylalkoxylates by the reaction of fluorinated alcohols with alkylene epoxides in the presence of a catalyst system.

BACKGROUND OF THE INVENTION

Alcohol alkoxylates are an important class of materials having use in a wide variety of industrial applications, for example as nonionic surfactants. They are typically prepared by the reaction of an alcohol with an alkylene epoxide such as ethylene oxide (i.e. oxirane) or propylene oxide (i.e. 2-methyloxirane) in the presence of one or more catalysts. Compositions prepared by the reaction of an alcohol incorporating a fluorinated alkyl group with an alkylene epoxide (fluoroalkylalkoxylates) are especially useful in several important industrial applications, including use as nonionic fluorosurfactants in the manufacture of PVC films, electrochemical cells, and various photographic coatings.

There are numerous known catalyst systems and processes for the alkoxylation of fluorinated alcohols. Lewis acids have been shown to be effective catalysts, e.g. boron trifluoride or silicon tetrafluoride, alone or in combination with metal hydrides, fluorides, alkyls or alkoxides. Unfortunately, such acidic materials also catalyze side reactions during the alkoxylation, such as dimerization of alkylene epoxides to form dioxanes. The side reactions lead to excess waste generation, product contamination, and higher consumption of reactants, thereby significantly increasing costs and making operation of the processes more difficult. While the use of strong bases as catalysts for the alkoxylation of hydrocarbon alcohols minimizes some side reactions, the use of strong base alone is not satisfactory for alkoxylation of flurorinated alcohols.

A commercially important class of fluoroalkoxylates consists of a mixture thereof derived by the alkoxylation of a commercial mixture of perfluoroalkylethanols having the general structure $R_fCH_2CH_2OH$ wherein $R_f$ is a linear or branched perfluoroalkyl group having from 4 to 30 carbon atoms. The mixture of perfluoroalkyl-ethanols is alkoxylated using strong base catalysts, alone or in combination with sodium borohydride. Unfortunately, that alkoxylation process is plagued with variability in respect of reaction rates and induction period which makes commercial manufacture of these fluoroalkoxylates unpredictable and difficult.

It is more convenient and economical to manufacture, store, and ship fluoroalkylalkoxylates in a solution of higher concentration, typically at about 40 percent by weight. In order to achieve this high solution concentration, known fluoroalkylalkoxylates must be dissolved in an organic solvent, such as isopropyl alcohol (IPA), or in a solvent mixture comprising water in combination with one or more of such organic solvents. However, the resulting solution may be flammable or have increased toxicity, and thus be more difficult and expensive to ship and use safely. In addition, the users of said fluoroalkylalkoxylate solutions frequently must remove the organic solvent during their manufacturing operations; this can be expensive and result in increased worker safety and environmental hazards. Even when dissolved in organic solvent mixtures, known fluoroalkylalkoxylates tend to form sediments. Such sediments are not easily filterable, and they tend to form continuously over time, which makes it impractical to remove the sediments from fluoroalkylalkoxylate solutions before shipment to the user. There are other fluoroalkylalkoxylates disclosed in the prior art which have higher water solubility, e.g. those having a large average number of the hydrophilic oxyalkylene groups, typically greater than about 18 such groups. Another example is Fluorotenside FT-219 marketed by Bayer AG; however, the structures of that product and related compositions incorporate additional hydrophilic functional groups, such as sulfonylamido linkages. In addition, a high degree of alkoxylation may result in the fluoroalkylalkoxylate composition forming a gel during preparation that makes them difficult or impossible to use.

BRIEF SUMMARY OF THE INVENTION

The present invention relates to a novel catalyst useful for the preparation of fluoroalkylalkoxylates. In particular, one reacts at least one fluorinated alcohol with at least one alkylene epoxide in the presence of a novel catalyst system comprising an iodine source and an alkali metal borohydride. In addition to its general usefulness for the preparation of mixtures of fluorinated alcohol alkoxylates, the catalyst system of this invention can be successfully employed for the alkoxylation of discrete perfluoroalkyl-ethanols.

DETAILED DESCRIPTION OF THE INVENTION

The process of the present invention comprises reacting a fluorinated alcohol or mixture of fluorinated alcohols with one or more alkoxylating agents in the presence of a catalyst system comprising a mixture of an alkali metal borohydride and at least one iodine source selected from the group consisting of alkali metal iodides, alkaline earth metal iodides, and elemental iodine at temperatures in the range between about 90° C. and 200° C. and pressures of from atmospheric pressure to about 100 psig. The catalyst system is effective in the absence of promoters or other catalysts such as strong bases, although such materials can be present if desired.

The alkali metal borohydrides suitable for use in the catalyst system of the present invention include sodium borohydride, potassium borohydride, and lithium borohydride, with sodium borohydride being preferred. The mole ratio of alkali metal borohydride to fluorinated alcohol can vary widely. Normally the mole ratio will be in the range between about 0.005 and 0.25 or higher, the upper limit being imposed only by practical considerations such as the cost of excessive borohydride use, contamination of product and waste streams with excess borohydride, and potential difficulty in controlling the rate of the exothermic alkoxylation reaction. The optimum mole ratio of borohydride to fluorinated alcohol may be determined by standard experimental methods familiar to those skilled in the art of alcohol alkoxylation reactions, and will be affected by such factors as the structures of the fluorinated alcohol and alkoxylating agent, and the temperature, pressure and cooling efficiency of the reaction vessel. For the reaction of an alkylene oxide, such as ethylene, with fluorinated alcohols useful for the purposes of this invention at 130° C. to 145° C. under atmospheric pressure, the preferred mole ratio is in the range between about 0.025 and about 0.1.

Iodine sources suitable for use in the catalyst system of the present invention include elemental iodine, lithium iodide, sodium iodide, potassium iodide, and calcium iodide. The preferred iodine source is iodine or sodium iodide or a mixture of the same. The mole ratio of iodine source to alkali metal borohydride is in the range between about 0.1 and about 300. The optimum mole ratio of iodine source to alkali metal borohydride may be determined by standard experimental methods familiar to those skilled in the art. For the reaction of an alkylene oxide with fluorinated alcohols useful for the purposes of this invention at 130° C. to 145° C. under atmospheric pressure, the preferred mole ratio is in the range between about 0.1 and about 0.5, and the most preferred mole ratio is in the range between about 0.1 and 0.3. At high levels of iodine source relative to borohydride, the alkoxylation reaction tends to be inhibited and the rate of reaction may slow. Inert materials or solvents may be also be present during the reaction, although in a preferred embodiment the fluorinated alcohol or alcohol mixture is reacted in neat form with the alkoxylating agent. It is also preferable that the fluorinated alcohol be thoroughly dried using methods known to those skilled in the art prior to reaction with the alkoxylating agent to avoid undesirable side reactions. Note that the process of the present invention could be successfully applied to the alkoxylation of non-fluorinated alcohols as well.

The fluorinated alcohols which can be alkoxylated using the process of the present invention include those compounds having the general formula:

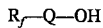

wherein $R_f$ is a linear or branched perfluoroalkyl group having from 4 to 20 carbon atoms, or a mixture of these groups;

Q is —(CH$_2$)$_n$—,

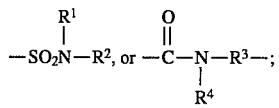

each of $R^1$ and $R^3$ is independently hydrogen or an alkyl group containing from 1–6 carbon atoms, preferably from 1–4 carbon atoms;

each of $R^2$ and $R^4$ is independently a divalent linear or branched alkylene group containing from 1–6 carbon atoms, preferably from 1–4 carbon atoms; and n is an integer in the range between 1 and 6, preferably 1 to 3.

More specifically, fluorinated alcohols which can be alkoxylated using the process of the present invention include those compounds having the following formulae:

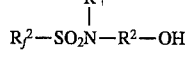

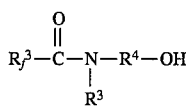

wherein $R_f^1$ is linear or branched perfluoroalkyl having from 4 to 20 carbon atoms; each of $R_f^2$ and $R_f^3$ is independently linear or branched perfluoroalkyl having from 4 to 12 carbon atoms, preferably from 6 to 10 carbon atoms; and $R^1$, $R^2$, $R^3$, $R^4$ and n are defined as given above. Mixtures of fluoroalcohols having the formula: $R_f^1$—(CH$_2$)$_n$—OH are used commercially in a variety of distributions, e.g. that given hereinbelow for the EXAMPLES.

In a preferred embodiment, fluoroalkylethoxylate compositions of the present invention are prepared by the reaction of a suitable fluorinated alcohol mixture with ethylene oxide in the presence of the above-described catalyst in accordance with the following equation:

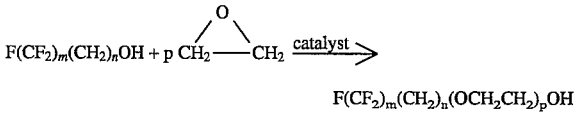

wherein n is an integer from about 4 to about 20, provided that the mixture contains at least 5 weight percent of molecules in which m is 8 or higher or mixtures of the same, but in no more than 5 weight percent of the molecules is m equal to 14 or higher or mixtures of the same;

n is an integer of from 1 to 3, preferably 2; and p is an integer of from about 1 and about 40, provided that the distribution of molecules in said mixture has an average p of from 8 to 17.

In respect of the length of the linear fluoroalkyl group in the molecules of the mixture (m), the compositions prepared in accordance with the process of the present invention comprise mixtures of molecules having m in the range between 2 and about 20. The percentage of molecules in the mixture having m equal to 8 or higher, or mixtures of the same, must be 5% by weight or greater; provided that no more than 5 weight percent of the molecules have m equal to 14 or higher or mixtures of the same; otherwise dilute water solutions of the fluoroalkylethoxylate will not have the beneficial property of relatively constant surface tension in the concentration range between 0.1 and 0.01 percent by weight of fluoroalkylethoxylate. The percentage of molecules in the fluoroalkylethoxylate mixture having m of 14 or higher, or mixtures of the same, must be 5 percent by weight or lower; otherwise water solutions of the fluoroalkylethoxylate will contain sediment and be turbid. Concerning the number of the linear alkylene linking groups, n, the compositions prepared in accordance with the process of the present invention comprise molecules having n equal to 1, 2, 3, or mixtures of the same, most preferably n is 2. With regard to the degree of ethoxylation, p, the compositions prepared in accordance with the process of the present invention comprise mixtures having a distribution of fluoroalkylethoxylate molecules having different numbers of oxyethylene units. This distribution may include molecules having from 1 to 40 oxyethylene units (p) clustered about a peak value of p and tapering off at higher and lower values of p. The distribution of p will have an average over all molecules in the mixture, referred to herein as the average degree of ethoxylation ($P_{average}$) in the range between about 8 and about 17. For a mixture having the distribution of fluoroalkyl groups defined hereinbelow, if $P_{average}$ is lower than about 8 the composition will have low water solubility. Alternatively, if the mixture has $P_{average}$ greater than about 17, water solutions of the mixture will not have adequate surface tension reduction to be useful as nonionic fluorosurfactants. The compositions prepared in accordance with the process of this invention comprise mixtures having $P_{average}$ in the range between about 12 and about 17. In addition to having enhanced solubility in water and adequate surfactant properties, water solutions of the fluoroalkylethoxylate compositions in which $P_{average}$ is between about 12 and 17 will possess the added advantage of upper cloud points (UCP) near 100° C. UCP refers to the temperature at which the fluorosurfactant forms a separate phase leading to higher solution surface tension and often cloudiness. A higher temperature UCP thus affords an enhanced temperature range of utility for use of the fluoroalkylethoxylate composition. Fluoroalkylethoxylate compositions of the present invention having $P_{average}$ lower than about 12 have much reduced UCP temperatures.

The catalyst is the above-described mixed system comprising an alkali metal borohydride in combination with at least one source of iodine selected from elemental iodine, an alkali metal iodide, or an alkaline earth metal iodide. The fluorinated alcohols useful as reactants in the process are well known; e.g. see U.S. Pat. No. 5,097,090 and patents cited in Col. 1 thereof (the USPTO file of that patent shows that "478,760" in Col. 1, line 19, should be "4,478,760"). Thus they may be prepared by methods known in the art, such as by the telomerization of tetrafluoroethylene in the presence of suitable catalysts followed by ethylation and hydrolysis to afford fluorinated alcohols having n equal to 2. The distribution of fluoroalkyl groups (i.e. distribution of m) in the fluoroalkylethoxylate product mixture will closely approximate the distribution of fluoroalkyl groups in the starting fluorinated alcohol mixture, and so the alcohol mixture used should be chosen to be close to that desired in the fluoroalkylethoxylate product. In a preferred embodiment, the fluoroalkylethoxylates are derived from mixtures of fluorinated alcohols which are prepared by telomerization of TFE and which have a distribution of m in the following ranges:

| m | percent by weight in mixture |
|---|---|
| 6 and lower | 0–70 |
| 8 | 20–60 |
| 10 | 5–40 |
| 12 | 1–25 |
| 14 and higher | 0–5 |

In a more preferred embodiment, the fluoroalkylethoxylates are derived from mixtures of fluorinated alcohols which are prepared by telomerization of TFE and which have a distribution of m in the following ranges:

| m | percent by weight in mixture |
|---|---|
| 6 and lower | 40–65 |
| 8 | 20–40 |
| 10 | 5–20 |
| 12 | 1–10 |
| 14 and higher | <3 |

The latter distribution is more preferred because it is similar to that produced in the commercial manufacture of these perfluoroalkyl ethanols, making them a more economical ingredient for the preparation of the fluoroalkylethoxylates of the present invention. Additional illustrative examples of fluorinated alcohols useful for the purposes of this invention include those given below.

In one embodiment, the perfluoroalkylethyl alcohol is mixture of the formula $F(CF_2)_mCH_2CH_2OH$, wherein m is predominantly 6, 8 and 10. In a typical mixture of such fluoroalcohols, the compounds will have the following approximate composition in relation to their $F(CF_2)_m$ radicals:

0% to 3% wherein m=4,
27% to 37% wherein m=6,
28% to 32% wherein m=8,
14% to 20% wherein m=10,
8% to 13% wherein m=12,
3% to 6% wherein m=14,
0% to 2% wherein m=16,
0% to 1% wherein m=18, and
0% to 1% wherein m=20.

A perfluoroalkylethyl alcohol mixture of the formula shown above wherein m is predominantly 8, 10 and 12. In a typical mixture of such fluoroalcohols, the compounds will have the following approximate composition in relation to their $F(CF_2)_m$ radicals:

0% to 3% wherein m=6,
45% to 58% wherein m=8,
26% to 32% wherein m=10,
10% to 14% wherein m=12,
2% to 5% wherein m=14,
0% to 2% wherein m=16,
0% to 1% wherein m=18, and
0% to 1% wherein m=20;

A perfluoroalkylmethyl alcohol of the formula $F(CF_2)_5CH_2OH$;

A N-alkyl-N-ethanolperfluoroalkylsulfonamide of the formula $F(CF_2)_mSO_2N(R)CH_2CH_2OH$ wherein R is methyl or propyl and m is 8; and Hexafluoroisopropanol.

The alkoxylation reactions of the present invention are normally carried out with materials or mixtures of materials comprising alpha and beta alkylene epoxides. Of these materials, ethylene oxide (i.e. oxirane), propylene oxide (i.e. 2-methyloxirane), and mixtures of these are preferred. Two or more alkylene oxides can be added as a mixture, or they can be added sequentially (first one and then another). Thus two or more alkylene oxides may be randomly distributed in the product or they can be clustered in one or more groups of each. Most preferred is the use of ethylene oxide alone due to the generally slower reactivity of alkylated epoxides such as propylene oxide.

The fluorinated alkoxylation products can have essentially any desired content of alkyloxy units. For example, in alcohol alkoxylations ethylene oxide will normally comprise from about 10% to 90% of the product composition by weight. However, for many purposes the content of ethylene oxide will be in the range between about 20% and about 70% by weight. The weight of alkoxylating agent present in the reaction mixture is not critical other than the minimum amount necessary to provide the number of alkyloxy units desired in the product must be present.

While the process of the present invention can be carried out at temperatures of from about 90° C. to about 200° C., for practical purposes, commercial operation of the process will be carried out in the temperature range between about 120° C. and about 170° C. The process can be carried out at ambient atmospheric pressure; however, pressures above or below ambient can be used as desired. It is essential only that sufficient pressure be used to maintain the alcohols present in the liquid phase during the alkoxylation. Normally, pressures of up to about 100 pounds per square inch gauge (psig) can be used, the upper limit being imposed primarily by convenience, cost, and the cooling efficiency of the reaction equipment. Reaction pressures in the range between ambient atmospheric pressure and about 50 psig are preferred, with operation in the pressure range between about 20 and about 50 psig especially preferred.

The process of the present invention allows much flexibility in the operation of the process. The alkali metal borohydride and iodine source can be added to the fluorinated alcohol prior to or during the addition of the alkoxylating agent. In a preferred embodiment, the fluorinated alcohol or mixture of fluorinated alcohols is mixed with the alkali metal borohydride and iodine source prior to addition of the alkoxylating agent and heating.

The following examples are provided in further illustration of the invention but not by way of limitation.

GENERAL ETHOXYLATION PROCEDURE FOR FLUORINATED ALCOHOLS

An appropriately sized glass flask is equipped with an agitator, a dry ice condenser, a subsurface gas inlet tube, and an inert nitrogen or argon atmosphere at ambient pressure. The desired amount of fluorinated alcohol is charged to the flask and then dehydrated by heating at 80° C. under a sparge of inert gas. The alkali metal borohydride and iodine source are then added and the mixture is stirred and heated to 140°–145° C. Charging of gaseous ethylene oxide is then initiated by bubbling the gas into the reaction subsurface through the gas inlet tube, the rate of addition being maintained so that a slow reflux of the ethylene oxide is observed in the condenser. Periodically the ethylene oxide feed may be interrupted and the reaction mixture weighed in order to determine the amount of ethylene oxide having reacted with the fluorinated alcohol.

Except as noted, the fluorinated alcohol employed in all of the following examples consisted of a mixture of fluoroalkylethanols having the general structure $F(CF_2)_mCH_2CH_2OH$ wherein m is an integer in the range between 4 and 20 and being distributed in the mixture at approximate weight percent concentrations of

| | |
|---|---|
| m = 2 to 4 | 4% |
| m = 6 | 35% |
| m = 8 | 30% |
| m = 10 | 17% |
| m = 12 | 8% |
| m = 14 or greater | 6% |

Except where noted, the alcohol mixture was purified prior to use by distillation or extraction with aqueous sodium hydroxide to ensure that no alkyl iodide contaminants were present in the fluorinated alcohol.

PROCEDURE FOR DETERMINATION OF SURFACTANT WATER SOLUBILITY

The water solubility of the fluoroalkylethoxylate compositions was determined by slowly adding the fluoroalkylethoxylate to 60 grams of distilled water at 25° C. with agitation provided by a magnetic stirring apparatus. The mass of fluoroalkoxylate added was measured during the addition, and the addition was continued until the development of solution turbidity was observed. The solubility is given by the weight percent of fluoroalkoxylate that may be added to the water before development of turbidity is observed.

PROCEDURE FOR DETERMINATION OF SOLUTION SURFACE TENSION

All surface tension measurements were made using a University of Texas model 500 Spinning Drop Interfacial Tensiometer. A solution of fluoroalkylethoxylate was prepared in distilled water and diluted to the desired concentration. The solution surface tension was then measured following the standard operating instructions supplied with the tensiometer.

PROCEDURE FOR DETERMINATION OF UPPER CLOUD POINT

Upper cloud point determinations were performed on fluoroalkylethoxylate solutions using a modified version of ASTM standard method D2024-65. A 1 gram sample of fluoroalkoxylate was dissolved in 100 milliliters of deionized water in a beaker. The beaker was placed on a hot plate and the solution was stirred and gradually heated until solution cloudiness was observed, the temperature of this occurrence being recorded as T1. The beaker was then removed from the hot plate and allowed to cool with continued stirring until the cloudiness disappeared, the temperature of this occurrence being recorded as T2. The upper cloud point was calculated as the average of T1 and T2 rounded to the nearest degree Celsius.

EXAMPLES 1 and 2

The general ethoxylation procedure was carried out using 244 grams (approx. 0.55 mole) of purified fluorinated alcohol and employing 1.02 grams (0.027 mole) of sodium borohydride and 1.8 grams (0.007 mole) of iodine as the catalyst system. In Example 1, ethylene oxide reacted rapidly with the fluorinated alcohol, with 328 grams of ethylene oxide being reacted in 7 hours at 140° C. The resulting fluoroalkyl ethoxylate product thus had an average of 14.9 ethylene oxide units per molecule. In Example 2, the procedure was repeated using the same reactant and catalyst loadings. Ethylene oxide reaction again occurred rapidly, with 441 grams of ethylene oxide being reacted in 6 hours at 140° C. to yield a fluoroalkyl ethoxylate product having an average of 20 ethylene oxide units per molecule.

EXAMPLE 3

To a 250 milliliter flask under an inert nitrogen atmosphere at 1 atmosphere pressure and equipped with a dry ice condenser and gas inlet was charged 60 grams (0.105 mole) of $F(CF_2)_8SO_2N(C_2H_5)CH_2CH_2OH$ (FC-10, available from the 3M company), 0.15 grams (0.004 mole) of sodium borohydride and 0.08 grams (0.0005 mole) of sodium iodide. The contents of the flask were heated to 105° C., and 5 grams (0.114 mole) of ethylene oxide gas was slowly fed into the flask. The reaction mixture was then heated to 143° C. and held for 4.75 hours. The mixture was allowed to cool to room temperature, the dry ice was removed from the condenser, and the reaction mixture was purged with nitrogen to remove unreacted ethylene oxide. Based on weight gain, 2 grams (0.045 mole) of ethylene oxide had added to the alcohol. An additional 0.24 grams (0.0016 mole) of sodium iodide and 0.27 grams (0.0011 mole) of iodine was added to the reaction vessel and the vessel was reheated to 110° C. Ethylene oxide addition was again started and the reaction vessel was heated to 148° C. and held for 5.7 hours during EO addition. A total of 24 grams (0.54 mole) of ethylene oxide was added. The product was allowed to cool to room temperature, the dry ice was removed from the condenser, the reaction mixture was purged with nitrogen for 12 hours to remove unreacted ethylene oxide, and the product mixture was neutralized with acetic acid. The product was $F(CF_2)_8SO_2N(C_2H_5)CH_2CH_2O(CH_2CH_2O)_{4.3}H$.

CONTROL A

The general ethoxylation procedure was carried out using 233 grams (approx. 0.53 mole) of purified fluorinated alcohol of Example 1 and employing 1.0 grams (0.024 mole) of sodium hydride as the catalyst. No reaction of ethylene oxide was observed after 3.5 hours at 145° C.

CONTROL B

The general ethoxylation procedure was carried out using 233 grams (approx. 0.53 mole) of purified fluorinated alcohol of Example 1 and employing 0.5 grams (0.012 mole) of sodium hydride and 0.5 grams (0.0033 mole) of sodium iodide as the catalyst system. After charging ethylene oxide and heating at 145° C. for 3.5 hours, essentially no reaction had occurred. An additional 0.5 gram (0.033 mole) of sodium iodide was then added and ethylene oxide addition continued, but still no ethylene oxide uptake was observed. At this point, 1.02 grams (0.027 mole) of sodium borohydride was added to the reaction mixture and rapid ethylene oxide reaction was then observed. A total of 252 grams of ethylene oxide reacted in 8.5 hours at 145° C.

CONTROL C

The general ethoxylation procedure was carried out using 233 grams (approx. 0.53 mole) of purified fluorinated alcohol of Example 1 and employing 0.5 grams (0.012 mole) of sodium hydride and 1.02 grams (0.027 mole) of sodium borohydride as the catalyst system. After heating at 145° C. and charging ethylene oxide for 9.5 hours, essentially no reaction had occurred. The reaction mixture was then cooled to 75° C. followed by the addition of 0.5 grams (0.0033 mole) of sodium iodide. The mixture was again heated to 145° C. and rapid ethylene oxide uptake was now observed. After 4 hours 70 grams of ethylene oxide had reacted, with an additional 180 grams reacting over the next 4 hours after the addition of an additional 0.5 grams of sodium iodide.

CONTROL D

The general ethoxylation procedure was carried out using 244 grams (approx. 0.55 mole) of purified fluorinated alcohol of Example 1 and employing 1.02 grams (0.027 mole) of sodium borohydride as the catalyst. After heating at 145° C. and charging ethylene oxide for 2.5 hours, essentially no reaction had occurred. The reaction mixture was then cooled to 80° C. followed by the addition of 1.8 grams (0.007 mole) of iodine. The mixture was again heated to 145° C. and rapid ethylene oxide uptake was now observed. After 5 hours 240 grams of ethylene oxide had reacted to afford a product having an average of 11 ethylene oxide units per molecule.

EXAMPLE 4

To a 250 milliliter flask under an inert nitrogen atmosphere at 1 atmosphere pressure and equipped with a dry ice condenser and gas inlet was charged 60 grams (approximately 0.145 mole) of a mixture composed of 54% $F(CF_2)_6CH_2CH_2OH$, 33% $F(CF_2)_8CH_2CH_2OH$, approximately 9.5% $F(CF_2)_{10}CH_2CH_2OH$, approximately 3.5% $F(CF_2)_{12}CH_2CH_2OH$, and less than 0.1% $F(CF_2)_mCH_2CH_2OH$ wherein m is 14 or greater. To that mixture was added 0.23 grams (0.04 mole) of sodium borohydride, 0.45 grams (0.02 mole) of sodium iodide, and 0.39 grams (0.01 mole) of iodine. The contents of the flask were heated to about 100° C., and 85 grams (1.93 moles) of ethylene oxide gas were slowly fed into the flask over 336 minutes, during which time the reaction temperature quickly rose to and remained at about 140° C. The reaction mixture was then allowed to cool to room temperature. After removing the dry ice from the condenser, the reaction mixture was purged with nitrogen for 12 hours to remove any residual ethylene oxide. The product was then neutralized with 0.36 grams (0.04 mole) of acetic acid. The yield of product was 95% (based on weight gain). The product was $F(CF_2)_mCH_2CH_2(OCH_2CH_2)_pOH$, wherein m is an integer in the range of 4 to 14; p is an integer in the range of 1 to 30 with an average of about 12. A clear, one phase solution was obtained when 40 g of this product was mixed with 60 g of water at room temperature.

By way of contrast, the water solubilities of several commercial fluoroalkylalkoxylates are shown in Table 1, from which it can be seen that they have very low solubilities in water, generally lower than 8 percent by weight.

TABLE 1

| Water Solubility of Commercial Fluoroalkylalkoxylates | | |
|---|---|---|
| Manufacturer | Product | Water-Solubility @25° C. |
| Hoechst | Afilon OTN | 0.1 |
| Ciba-Geigy | S-107B | 0.1 |
| Asahi Glass | S-141 | <5 |
| DuPont | Zonyl FSN-100 | 8 |
| Daikin | DS-401 | <1 |

EXAMPLES 5-9 & Control E & F

The fluoroalkylethoxylate compositions of Examples 5 through 9 and Controls E and F were prepared in a manner similar to Example 4 as described in Table 2. The fluorinated alcohol mixture employed for each of Examples 5 through 9 and Controls E and F was similar to that of Example 4.

TABLE 2

| Reaction Conditions for Examples 5–9 & Controls E & F | | | | | | | |
|---|---|---|---|---|---|---|---|
| Example [Control] | mole $R_fOH$ | mole EO | mole NaI | mole $I_2$ | mole $NaBH_4$ | Temp, °C. | Time, h |
| [E] | 0.144 | 0.979 | 0.0007 | 0 | 0.006 | 143 | 4.7 |
| [F] | 0.144 | 1.044 | 0.0007 | 0 | 0.006 | 145 | 5.0 |
| 5 | 0.144 | 1.166 | 0.0007 | 0 | 0.006 | 145 | 4.4 |
| 6 | 0.140 | 1.428 | 0.003 | 0.001 | 0.006 | 149 | 5.2 |
| 7 | 0.150 | 1.815 | 0.003 | 0.002 | 0.006 | 138 | 4.8 |
| 8 | 0.180 | 2.484 | 0.004 | 0.002 | 0.007 | 143 | 6.3 |
| 9 | 0.140 | 2.436 | 0.003 | 0.001 | 0.006 | 145 | 4.5 |

TABLE 3

Water Solubility and Solution Characteristics of Fluoroalkyl-
ethoxylate Products of Examples 5–9 & Controls E & F

| Example [Control] | Avg EO Number ($P_{average}$) | Water Solubility (wt. percent) | Water Solution Turbidity |
|---|---|---|---|
| [E] | 6.8 | <1 | 2 liq. phases |
| [F] | 7.2 | <1 | 2 liq. phases |
| 5 | 8.1 | >40 | Clear |
| 6 | 10.2 | >40 | Clear |
| 7 | 12.1 | >40 | Clear |
| 8 | 13.8 | >40 | Clear |
| 9 | 17.4 | >40 | Clear |

The data set forth in Table 3 indicate that only fluoroalkylethoxylate compositions having an average EO number of 8 or greater exhibit enhanced water solubility.

Samples of the fluoroalkylethoxylate products from Examples 5 through 9 were dissolved in water and diluted to final concentrations of 0.1, 0.01, and 0.001 percent fluoroalkylethoxylate by weight. The surface tensions of these solutions were then determined, and the results are shown in Table 4 along with upper cloud point data for these products.

TABLE 4

Water Solution Surface Tension and Upper Cloud Point for
Fluoroalkylethoxylate Products of Examples 5–9

| Example | Avg EO Number ($P_{average}$) | Water Solution Surface Tension (dyne/cm) at indicated concentration | | | UCP, °C. |
|---|---|---|---|---|---|
| | | 0.1 wt % | 0.01 wt % | 0.001 wt % | |
| 5 | 8.1 | 16 | 16 | 20 | no data |
| 6 | 10.2 | 19 | 19 | 27 | 80 |
| 7 | 12.1 | 21 | 21 | 26 | >98 |
| 8 | 13.8 | 22 | 23 | 29 | >99 |
| 9 | 17.4 | 28 | 28 | 35 | >100 |

The data of Table 4 show that the surface tensions of solutions of the fluoroalkoxylate composition are constant across the concentration range of 0.01 to 0.1 percent by weight for all shown compositions. The solution surface tension does increase with increasing average EO number until the surface tension approaches the upper useful limit for fluorosurfactants of 30 dyne/cm when the EO number is 17.4 as in Example 9. In addition, it may be seen that the upper cloud points of the fluoroalkoxylates also increase with increasing EO number, approaching values near 100° C. when the average EO number is 12 or higher. Even at an average EO number of 8 as in Example 5, however, the UCP is sufficiently high to be useful for many applications.

EXAMPLE 10 & Controls G & H

The fluoroalkylethoxylate compositions of Example 10 and Controls G & H were prepared in a manner similar to Example 4 as described in Table 5. The fluorinated alcohol mixture employed for each of Example 10 and Controls G & H was similar to that of Example 4, except that the mixture was spiked with samples of pure $F(CF_2)_mCH_2CH_2OH$ where m is 14, 16, and 18 to give the concentrations of these compounds as indicated in the key to Table 5. Water solutions of the fluoroalkylethoxylates of Examples 10 and Controls G & H were prepared by mixing 40 grams of ethoxylate in 60 grams of water. The resulting characteristics of these solutions are described in Table 6.

TABLE 5

Reaction Conditions for Example 10 & Controls G & H

| Example [Control] | mole $R_fOH$ | mole EO | mole NaI | mole $I_2$ | mole $NaBH_4$ | Temp, °C. | Time |
|---|---|---|---|---|---|---|---|
| 10[a] | 0.139 | 1.751 | 0.003 | 0.001 | 0.006 | 145 | 4.2 |
| [G][b] | 0.136 | 1.822 | 0.003 | 0.001 | 0.005 | 145 | 5.5 |
| [H][b] | 0.132 | 2.112 | 0.0007 | 0 | 0.005 | 145 | 7.8 |

(a) composition same as Example 4, but spiked to give:
$F(CF_2)_{14}CH_2CH_2OH$   3.0%
$F(CF_2)_{16}CH_2CH_2OH$   1.4%
$F(CF_2)_{18}CH_2CH_2OH$   0.5%
(b) composition same as Example 4, but spiked to give:
$F(CF_2)_{14}CH_2CH_2OH$   3.6%
$F(CF_2)_{16}CH_2CH_2OH$   1.6%
$F(CF_2)_{18}CH_2CH_2OH$   0.6%

TABLE 6

Water Solution Characteristics of Fluoroalkylethoxylate
Products of Example 10 & Controls G & H

| Example [Control] | Avg EO Number ($P_{average}$) | Water Solution Sediment | Water Solution Turbidity |
|---|---|---|---|
| 10 | 12.6 | No | Clear |
| [G] | 13.4 | Yes | Cloudy |
| [H] | 16.0 | Yes | Cloudy |

It is apparent from the data of Table 6 that the enhanced water solubility of the fluoroalkoxylate compositions of the present invention is diminished when the composition includes greater than 5% of molecules having m equal to 14 and higher as in Controls G & H.

EXAMPLE 11 & CONTROL I

The fluoroalkylethoxylate compositions of Example 11 & Control I were prepared in a manner similar to Example 4 as described in Table 7. The fluorinated alcohol mixture employed for Control E consisted of 97% $F(CF_2)_6CH_2CH_2OH$ and 3% $F(CF_2)_8CH_2CH_2OH$ by weight, while that employed for Example 8 consisted of 95% $F(CF_2)_6CH_2CH_2OH$ and 5% $F(CF_2)_8CH_2CH_2OH$ by weight. The average degree of ethoxylation ($P_{average}$) was 12.8 and 12.6, respectively. The fluoroalkylethoxylate products of both Example 11 and Control I were soluble in water to greater than 40 percent by weight, said solutions having no sediment and being clear. Samples of each fluoroalkylethoxylate product were dissolved in distilled water and diluted to concentrations of 0.1 and 0.01 percent fluoroalkylethoxylate by weight. The surface tensions of the resulting solutions were measured, and are shown in Table 8.

EXAMPLE 12

The general ethoxylation procedure was carried out using 416 grams (approx. 1.0 mole) of fluorinated alcohol (Telomer BL Alcohol, not purified to remove Telomer B Iodides, and having the formula $F(CF_2)_nCH_2CH_2OH$, wherein n has the distribution: 5.7% n=4 and lower, 55.5% n=6, 26.4% n=8, 8.5% n=10, and 3.9% n=12 and higher) and employing 2.04 grams (0.054 mole) of sodium borohydride and 1.8 grams (0.007 mole) of iodine as the catalyst system. The ethylene oxide reacted rapidly with the fluorinated alcohol, with 239 grams of ethylene oxide being reacted in 5 hours at 140° C. The resulting fluoroalkyl ethoxylate product had an average of 5.4 ethylene oxide units per molecule.

TABLE 7

Reaction Conditions for Example 11 & Control I

| Example [Control] | mole $R_fOH$ | mole EO | mole NaI | mole $I_2$ | mole $NaBH_4$ | Temp, °C. | Time |
|---|---|---|---|---|---|---|---|
| [I][a] | 0.132 | 1.70 | 0.003 | 0.001 | 0.005 | 145 | 5.5 |
| 11[b] | 0.139 | 1.75 | 0.003 | 0.001 | 0.006 | 145 | 4.2 |

([a]) fluorinated alcohol mixture composed of 97% $F(CF_2)_6CH_2CH_2OH$ and 3% $F(CF_2)_8CH_2CH_2OH$;
([b]) fluorinated alcohol mixture composed of 95% $F(CF_2)_6CH_2CH_2OH$ and 5% $F(CF_2)_8CH_2CH_2OH$.

TABLE 8

Water Solution Surface Tension for Fluoroalkylethoxylate Products of Example 11 And Control I

| Example [Control] | Weight Percent $F(CF_2)_8CH_2CH_2OH$ | Water Solution Surface Tension (dyne/cm) at indicated concentration | |
|---|---|---|---|
| | | 0.1 wt % | 0.01 wt % |
| [I] | 3 | 23 | 29 |
| 11 | 5 | 24 | 24 |

It is apparent from Table 8 that the composition of Control I, which has 97% by weight of molecules wherein m is below 8, does not exhibit constant surface tension with varying water solution concentration between 0.01 and 0.1 percent by weight. However, when the composition is adjusted in Example 11 to one having only 95% of molecules with m below 8, constant surface tension across this concentration range is again observed.

We claim:

1. A process for the preparation of fluoroalkyl alkoxylates comprising reacting a fluorinated alcohol with an alkylene epoxide having 2 to 10 carbon atoms, or mixture of said alkylene epoxides, at a temperature from 90° C. to 200° C. and a pressure from ambient atmospheric pressure to 100 psig in the presence of an alkali metal borohydride present at a molar ratio of alkali metal borohydride to fluorinated alcohol of at least 0.005, and at least one iodine source selected from the group consisting of an alkali metal iodide, an alkaline earth metal iodide, elemental iodine, and mixtures of the same, at a molar ratio of iodine source to alkali metal borohydride of from 0.1:1.0 to 300:1; said fluorinated alcohol having the general formula:

$$R_f\text{—}Q\text{—}OH$$

wherein $R_f$ is a linear or branched perfluoroalkyl group having from 4 to 20 carbon atoms, or a mixture of these groups;

Q is 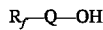,

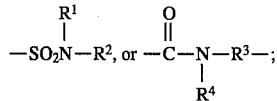

each of $R^1$ and $R^4$ is independently hydrogen or an alkyl group containing from 1–6 carbon atoms;

each of $R^2$ and $R^3$ is independently a divalent linear or branched alkylene group containing from 1–6 carbon atoms; and n is an integer of from 1 to 6.

2. The process of claim 1 wherein the fluorinated alcohol has the structure $R_fCH_2CH_2OH$ in which $R_f$ is a linear perfluoroalkyl group having from 4 to 20 carbon atoms, or a mixture of these groups.

3. The process of claim 1 wherein said alkylene epoxide is ethylene oxide or propylene oxide or a mixture thereof.

4. The process of claim 1 wherein said alkylene epoxide is ethylene oxide.

5. The process of claim 1 wherein said alkali metal borohydride is sodium borohydride.

6. The process of claim 1 wherein the molar ratio of alkali metal borohydride to fluorinated alcohol is from 0.25:1 to 0.1:1.

7. The process of claim 1 wherein said iodine source is elemental iodine, sodium iodide or a mixture thereof.

8. The process of claim 1 wherein the molar ratio of iodine source to alkali metal borohydride is from 0.1:1 to 0.5:1.

9. The process of claim 1 wherein the molar ratio of iodine source to alkali metal borohydride is from 0.1:1 to 0.3:1.

10. A process for preparing a mixture of fluoroalkylethoxylates which comprises reacting ethylene oxide with a perfluoroalkylalkanol in accordance with the following equation:

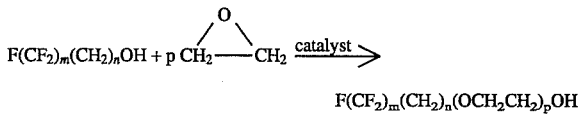

$$F(CF_2)_m(CH_2)_n(OCH_2CH_2)_pOH$$

wherein $F(CF_2)m$- is a linear perfluoroalkyl group;

m is an integer from about 4 to about 20, provided that the mixture contains at least 5 weight percent of molecules in which m is 8 or higher or mixtures of the same, but in no more than 5 weight percent of the molecules is m equal to 14 or higher, or mixtures of the same;

n is an integer from 1 to 3;

p is an integer from about 2 to about 40, provided that the distribution of molecules in said mixture has an average p from 8 to 17; and the catalyst consists essentially of a mixture of an alkali metal borohydride and at least one source of iodine selected from the group consisting of elemental iodine, alkali metal iodides and alkaline earth metal iodides.

11. The process of claim 10 where n is 2.

12. The process of claim 10 wherein the average of p in the molecular distribution of the mixture is from about 12 to about 17.

13. The process of claim 12 wherein n is 2.

14. The process of either claim 10, 11, 12 or 13 wherein said source of iodine is elemental iodine.

15. The process of either claim 10, 11, 12 or 13 wherein said source of iodine is sodium iodide.

16. The process of either claim 10, 11, 12 or 13 wherein said source of iodine is a mixture of elemental iodine and sodium iodide.

* * * * *